US010278564B2

(12) United States Patent
Kogiso et al.

(10) Patent No.: US 10,278,564 B2
(45) Date of Patent: May 7, 2019

(54) ENDOSCOPE TREATMENT SYSTEM

(71) Applicant: OLYMPUS CORPORATION, Tokyo (JP)

(72) Inventors: Junichi Kogiso, Tokyo (JP); Shotaro Takemoto, Tokyo (JP); Nobuko Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 146 days.

(21) Appl. No.: 14/945,141

(22) Filed: Nov. 18, 2015

(65) Prior Publication Data

US 2016/0073859 A1 Mar. 17, 2016

Related U.S. Application Data

(63) Continuation of application No. PCT/JP2014/078718, filed on Oct. 29, 2014.

(30) Foreign Application Priority Data

Nov. 1, 2013 (JP) .................................. 2013-228545

(51) Int. Cl.
*A61B 1/00* (2006.01)
*A61B 18/14* (2006.01)
(Continued)

(52) U.S. Cl.
CPC ........ *A61B 1/00087* (2013.01); *A61B 1/0014* (2013.01); *A61B 1/00089* (2013.01);
(Continued)

(58) Field of Classification Search
CPC .......... A61B 1/00101; A61B 17/00234; A61B 1/0014
(Continued)

(56) References Cited

U.S. PATENT DOCUMENTS

2001/0053909 A1 12/2001 Nakada et al.
2004/0158124 A1* 8/2004 Okada ................... A61B 1/012
600/104
(Continued)

FOREIGN PATENT DOCUMENTS

EP 2443988 A1 4/2012
GB 2492325 A 1/2013
(Continued)

OTHER PUBLICATIONS

Feb. 10, 2015 International Search Report issued in International Patent Application No. PCT/JP2014/078718.
(Continued)

*Primary Examiner* — Alexandra L Newton
*Assistant Examiner* — Rynae Boler
(74) *Attorney, Agent, or Firm* — Oliff PLC

(57) ABSTRACT

An endoscope auxiliary tool includes a first support section which is formed to extend along a longitudinal axis, a second support section which is formed substantially in parallel to the longitudinal axis of the first support section, a first protrusion section and a second protrusion section which are formed at distal end sections of the first support section and the second support section, respectively, and disposed more distal than the distal end section of the endoscope to sandwich an axis of a channel having an opening at the distal end section of the endoscope, and a positioning section which is configured to position the first protrusion section and the second protrusion section with respect to the distal end section of the endoscope such that the first support section and the second support section are inclined to the axis of the channel.

20 Claims, 10 Drawing Sheets

(51) Int. Cl.
*A61B 17/02* (2006.01)
*A61B 17/00* (2006.01)
*A61B 1/005* (2006.01)
*A61B 1/012* (2006.01)

(52) U.S. Cl.
CPC ...... *A61B 1/00098* (2013.01); *A61B 1/00101* (2013.01); *A61B 18/1492* (2013.01); *A61B 1/005* (2013.01); *A61B 1/012* (2013.01); *A61B 17/0218* (2013.01); *A61B 2017/00269* (2013.01); *A61B 2017/00296* (2013.01)

(58) Field of Classification Search
USPC .......................................... 600/104, 127, 129
See application file for complete search history.

(56) References Cited

U.S. PATENT DOCUMENTS

| | | | |
|---|---|---|---|
| 2005/0137453 A1 | 6/2005 | Ouchi et al. | |
| 2008/0132759 A1 | 6/2008 | Miyamoto et al. | |
| 2008/0177135 A1 | 7/2008 | Muyari et al. | |
| 2010/0030019 A1 | 2/2010 | Kuroda et al. | |
| 2010/0113878 A1 | 5/2010 | Kawano | |
| 2012/0101337 A1* | 4/2012 | Clark | A61B 1/00091 600/157 |
| 2012/0101338 A1* | 4/2012 | O'Prey | A61B 1/126 600/157 |

FOREIGN PATENT DOCUMENTS

| | | |
|---|---|---|
| JP | 2002045369 A | 2/2002 |
| JP | 2005224262 A | 8/2005 |
| JP | 2006231029 A | 9/2006 |
| JP | 2007-130167 A | 5/2007 |
| JP | 2009-247550 A | 10/2009 |
| JP | 4674975 B2 | 4/2011 |
| JP | 4847354 B2 | 12/2011 |
| JP | 2012040108 A | 3/2012 |
| JP | 4929453 B2 | 5/2012 |
| JP | 5231348 B2 | 7/2013 |
| JP | 5256491 B2 | 8/2013 |
| JP | 2013183933 A | 9/2013 |
| WO | 2006064868 A1 | 6/2006 |

OTHER PUBLICATIONS

Aug. 8, 2017 Search Report issued in European Patent Application No. 14859098.7.

Feb. 12, 2019 Office Action issued in European Patent Application No. 14859098.7.

* cited by examiner

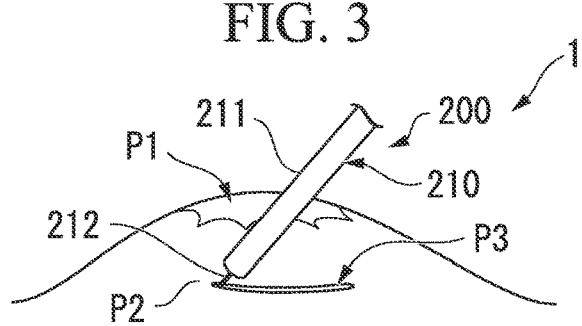
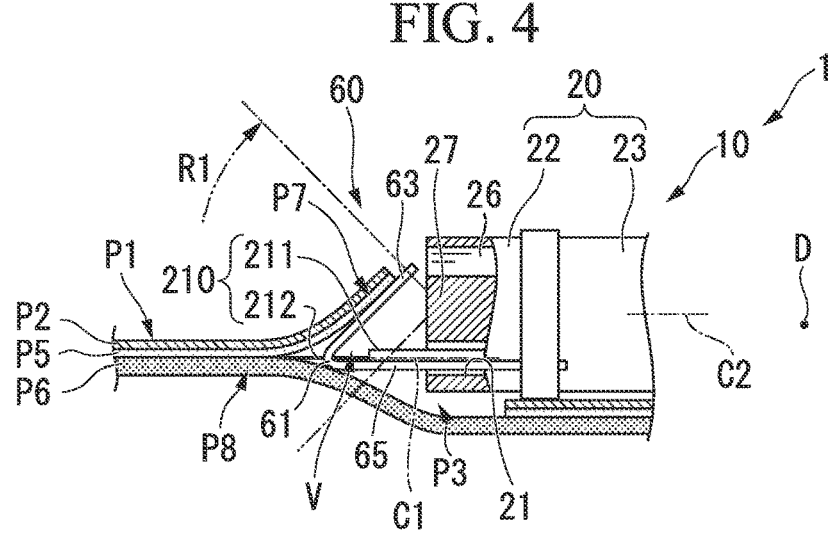
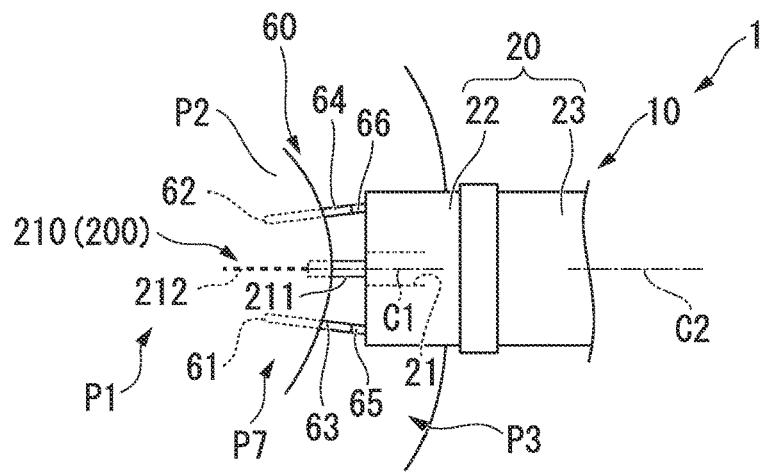

ENDOSCOPE TREATMENT SYSTEM

This application is a continuation application based on a PCT International Application No. PCT/W2014/078718, filed on Oct. 29, 2014, whose priority is claimed on Japanese Patent Application No. 2013-228545, filed on Nov. 1, 2013.

The contents of the PCT International Application and the Japanese Patent Application are incorporated herein by reference.

BACKGROUND OF THE INVENTION

Field of the Invention

The present invention relates to an endoscope treatment system used with a high frequency knife and configured to perform incision treatment.

Description of Related Art

In the related art, attachment of an endoscope auxiliary tool to a distal end section of an insertion section of an endoscope to improve a function of the endoscope is being investigated.

For example, in an endoscope treatment system disclosed in Japanese Unexamined Patent Application, First Publication No. 2002-45369, a hood for an endoscope serving as an endoscope auxiliary tool is attached to the distal end section of the insertion section of the endoscope. A transparent cap section having a substantially cylindrical shape and an endoscope mounting section having a substantially cylindrical shape are formed at the hood for an endoscope. The endoscope mounting section detachably fixes the hood for an endoscope to the distal end section of the insertion section of the endoscope.

An endoscope locking section that protrudes inward is formed at a distal end section of the endoscope mounting section. A claw section that protrudes inward is formed at a distal end section of the cap section.

In the endoscope treatment system disclosed in Japanese Unexamined Patent Application, First Publication No. 2002-45369 having the above-mentioned configuration, as the distal end of the insertion section of the endoscope is pushed into a position at which the distal end contacts with the endoscope locking section, the endoscope mounting section of the hood for an endoscope is fixed to the distal end of the insertion section of the endoscope, in a state in which the distal end of the insertion section of the endoscope does not enter the cap section. The distal end opening section of the cap section of the hood for an endoscope is pressed against the mucosa of the mucosa excision portion as a target.

An operator pushes out a snare wire in a state in which the distal end section of the snare wire protruded from a snare sheath abuts the claw section. The snare wire is expanded on a circumference along an inner circumferential surface of the distal end section of the cap section, and is disposed at the base of a raised excision portion of the mucosa.

Next, the operator pulls the snare wire into the snare sheath, and tightly binds the base of the excision portion of the mucosa. Next, the operator excises the mucosa by applying high frequency waves to the snare wire.

Meanwhile, a high frequency knife is introduced into a body cavity through a channel formed in the insertion section of the endoscope, and endoscopic submucosal dissection (ESD) of dissecting the affected mucosa portion is performed using the high frequency knife.

In the endoscopic submucosal dissection, for example, the operator endoscopically introduces an injection needle into the body cavity through the channel of the endoscope. Next, the operator injects a physiological saline solution into a submucosal layer of an affected mucosa portion using an injection needle to raise the affected mucosa portion. Further, the operator mounts an return electrode plate on a patient, and endoscopically introduces the high frequency knife having a known needle-shaped electrode. Next, the operator applies electricity to the electrode and raises the electrode around the affected mucosa portion, and the submucosal layer around the affected mucosa portion is incised when the electrode is moved along a periphery of the affected mucosa portion in the lateral direction.

SUMMARY OF THE INVENTION

According to a first aspect of the present invention, an endoscope auxiliary tool attached to a distal end section of an endoscope tool includes: a first support section which is formed to extend along a longitudinal axis; a second support section which is formed substantially in parallel to the longitudinal axis of the first support section; a first protrusion section and a second protrusion section which are formed at distal end sections of the first support section and the second support section, respectively, and disposed more distal than the distal end section of the endoscope to sandwich an axis of a channel having an opening at the distal end section of the endoscope; and a positioning section configured which is configured to position the first protrusion section and the second protrusion section with respect to the distal end section of the endoscope such that the first support section and the second support section are inclined to the axis of the channel.

According to a second aspect of the present invention, in the endoscope treatment auxiliary tool according to the first aspect, the endoscope auxiliary tool may further include a first pressing section which includes a distal end section continuing to the first protrusion section, extends toward a proximal end side of the endoscope auxiliary tool, and includes a proximal end attached to the distal end section of the endoscope; and a second pressing section which includes a distal end section continuing to the second protrusion section, extends toward the proximal end side, and includes a proximal end attached to the distal end section of the endoscope.

According to a third aspect of the present invention, in the endoscope auxiliary tool according to the first aspect, the endoscope auxiliary tool may further include a plate-shaped member attached to each of the first support section and the second support section, and disposed in an area that does not include the axis of the channel.

According to a fourth aspect of the present invention, in the endoscope auxiliary tool according to the first aspect, the endoscope auxiliary tool may further include a connecting section connected to a proximal end section of the first support section and a proximal end section of the second support section, respectively; and a plate-shaped member disposed more distal than the first support section and the second support section, configured to be capable of abutting the first support section and the second support section, and rotatably supported by the connecting section.

According to a fifth aspect of the present invention, in the endoscope auxiliary tool according to the third aspect, the plate-shaped member may be formed of a transparent material.

According to a sixth aspect of the present invention, in the endoscope auxiliary tool according to the fourth aspect, the plate-shaped member may be formed of a transparent material.

According to a seventh aspect of the present invention, an endoscope treatment system includes an endoscope which includes a flexible insertion section and a channel having an opening at a distal end surface of the insertion section; and an endoscope auxiliary tool which is attached to a distal end section of the insertion section. The endoscope auxiliary tool includes a first protrusion section and a second protrusion section disposed more distal than the distal end surface of the insertion section to sandwich an axis of the channel; a first support section which includes a distal end section continuing to the first protrusion section, extends toward the distal end surface so as to be inclined with respect to the axis of the insertion section, and includes a proximal end section attached to the insertion section; and a second support section which includes a distal end section continuing to the second protrusion section, extends toward the distal end surface side so as to be inclined at the same side as the first support section with respect to the axis of the insertion section, and includes a proximal end section attached to the insertion section.

BRIEF DESCRIPTION OF DRAWINGS

FIG. 3 is a view showing a procedure using the endoscope treatment system according to the first embodiment of the present invention.

FIG. 4 is a view showing a procedure using the endoscope treatment system according to the first embodiment of the present invention.

FIG. 5 is a plan view showing a procedure using the endoscope treatment system according to the first embodiment of the present invention.

DETAILED DESCRIPTION OF THE INVENTION

First Embodiment

Hereinafter, a first embodiment of an endoscope treatment system according to the present invention will be described with reference to FIGS. 1 to 7. Further, in all of the following drawings, to facilitate understanding of the drawings, the ratios of dimensions of components may be appropriately different from each other.

Figure 1:
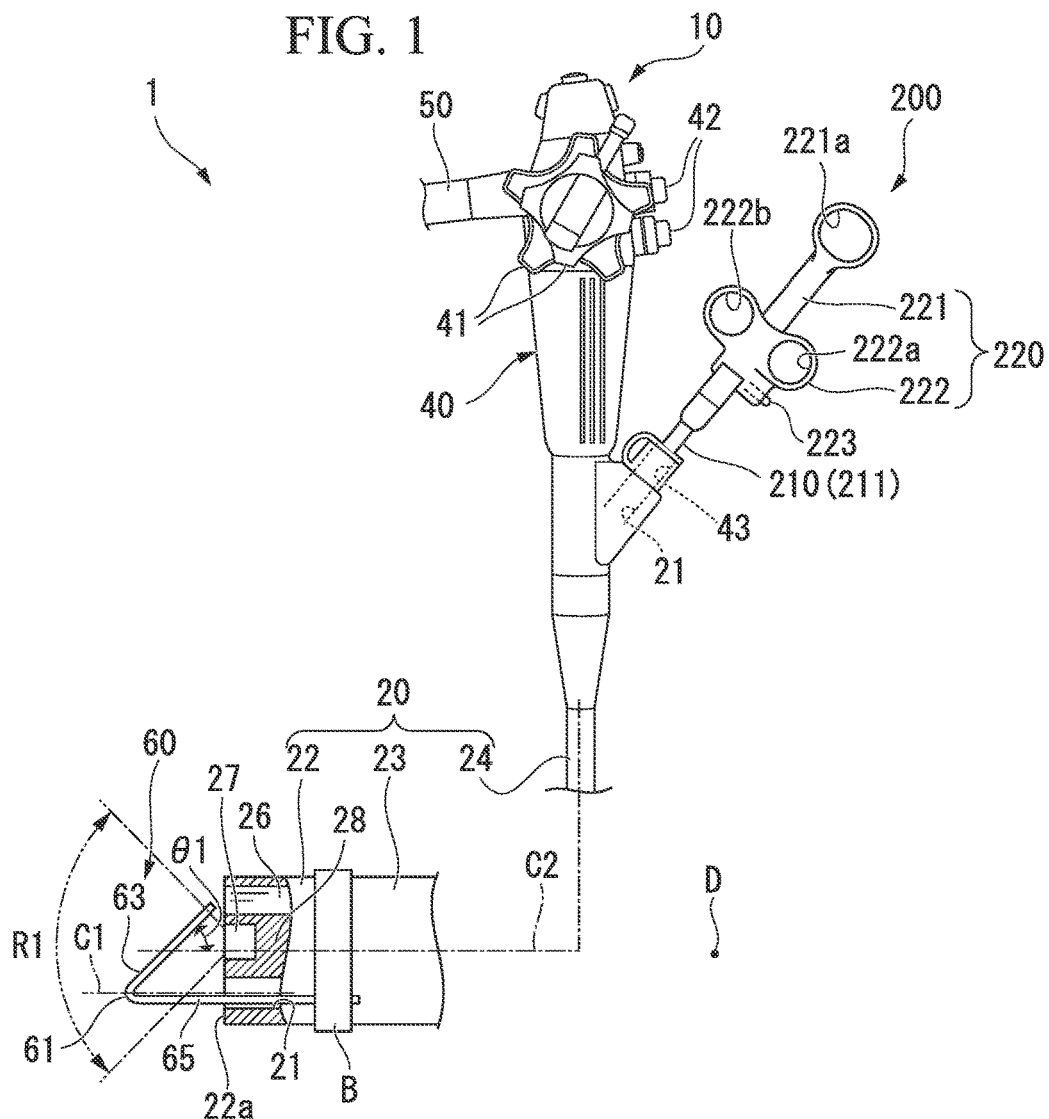
FIG. 1 is a general view showing an endoscope treatment system according to a first embodiment of the present invention, a portion of which is not shown.
Figure 2:
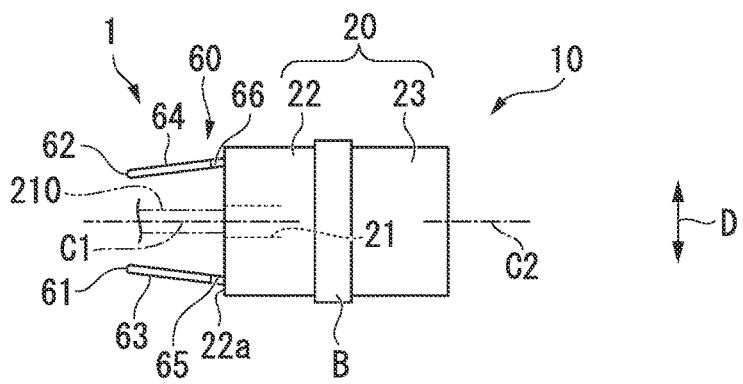
FIG. 2 is a plan view of a distal end section of the endoscope treatment system according to the first embodiment of the present invention.

As shown in FIGS. 1 and 2, an endoscope treatment system 1 of the embodiment includes an endoscope 10 and an endoscope auxiliary tool 60. The endoscope 10 has a flexible insertion section 20, and a channel 21 opened at a distal end surface 22a of the insertion section 20 is formed. The endoscope auxiliary tool 60 is attached to a distal end section of the insertion section 20.

The distal end section of the insertion section 20 of FIG. 1 is shown in a side view, a portion of which is not shown. The distal end section of the insertion section 20 of FIG. 2 is shown in a plan view. That is, as shown in FIG. 2, a light guide 26 (described below) is disposed at an upper side, and the channel 21 is disposed at a lower side. In all of the following drawings, as shown in FIG. 1, a surface when seen in a perpendicular direction D (described below) is referred to as a side surface, and a surface when seen in the same direction as the direction shown in FIG. 2 is referred to as a flat surface.

The endoscope 10 is a so-called direct viewing type soft device that can observe a forward side of the insertion section 20. The endoscope 10 includes the above-mentioned elongated insertion section 20, a manipulation section 40 installed at the proximal end section of the insertion section 20, and a universal cable 50 having one end section attached to a side surface of the manipulation section 40.

The insertion section 20 has a distal end rigid section 22 formed at a distal end, a curved section 23 attached to the proximal end section of the distal end rigid section 22 so as to be curved and manipulated, and a flexible tube section 24 having flexibility and attached to the proximal end section of the curved section 23.

The light guide 26 formed of a bundle of optical fibers and an observation unit 27 are formed at the distal end surface 22a of the distal end rigid section 22 and are exposed to the outside. The observation unit 27 has an objective lens and a charge coupled device (CCD), which are not shown.

The light guide 26 is inserted into the insertion section 20 and the manipulation section 40, and extends to the universal cable 50. The objective lens images an image of the observation target in a field of vision range R1 in front of the distal end surface 22a on a light receiving surface of the CCD. The CCD converts the image of the observation target in the field of vision range R1 into a signal displayed as an image, and transmits the converted signal to a signal wiring 28. The signal wiring 28 is inserted into the insertion section 20 and the manipulation section 40, and extends to the universal cable 50.

The channel 21 is inserted into the insertion section 20 and extended to the manipulation section 40. At the distal end side of the insertion section 20, an axis C1 of the channel 21 (hereinafter referred to as "a first axis C1") is parallel to an axis C2 of the insertion section 20 (hereinafter referred to as "a second axis C2").

In the curved section 23, a plurality of curved pieces (not shown) are connected in the second axis C2 direction. A distal end section of the manipulation wire is attached to the curved piece closest to the distal end. A proximal end side of the manipulation wire is inserted into the flexible tube section 24 and extended to the manipulation section 40.

An angle knob 41 configured to pull or push the manipulation wire, and a switch 42 are installed at the manipulation section 40. The switch 42 is configured to manipulate a light source, a monitor, a power supply, and so on, (not shown), which will be described below. As the angle knob 41 is manipulated, the manipulation wire can be manipulated to curve the curved section 23 in a desired direction.

A forceps port 43 in communication with the channel 21 is installed at the distal end side of the manipulation section 40.

A light source, a monitor and a power supply are connected to the end section of the universal cable 50. The light source supplies illumination light to a proximal end surface of the light guide 26. A signal processing circuit is installed in the monitor, and the signal wiring 28 is connected to the monitor. As a signal transmitted through the signal wiring 28 is converted by the signal processing circuit, the image in the field of vision range R1 of the observation target acquired by the CCD is displayed on the monitor.

The power supply supplies power to the CCD, the light source, the monitor, and so on, of the observation unit 27.

The endoscope auxiliary tool 60 has a first protrusion section 61 and a second protrusion section 62 (hereinafter referred to as "the protrusion sections 61 and 62"), a first support section 63 having a longitudinal axis and a second support section 64 extending substantially in parallel to the first support section 63 (hereinafter referred to as "the support sections 63 and 64"). The first protrusion section 61 and the second protrusion section 62 are disposed closer to the distal end of the endoscope auxiliary tool 60 than the distal end surface 22a of the insertion section 20. The first support section 63 is formed in a rod shape, and a distal end is configured to continue to the first protrusion section 61.

The second support section 64 is formed in a rod shape, and a distal end is configured to continue to the second protrusion section 62. The protrusion sections 61 and 62 of the embodiment are folded portions obtained by folding the distal end sections of first support section 63 and the second support section 64. Since the folded portions are disposed closer to the distal side than the distal end section of the endoscope and positioned with respect to the distal end section of the endoscope, the distal end section of the endoscope slips between a submucosal layer P5 and a muscle layer P6.

As shown in FIG. 2, in the perpendicular direction D perpendicular to the second axis C2, the protrusion sections 61 and 62 (the distal end sections of the first support section 63 and the second support section 64) are configured to sandwich the first axis C1 closer to the distal side than the distal end section of the endoscope. In the embodiment, when seen in the perpendicular direction D shown in FIG. 1, the protrusion sections 61 and 62 are disposed on the first axis C1. Specifically, the distal end sections of the first support section 63 and the second support section 64 sandwich the first axis C1 closer to the distal side than the distal end section of the endoscope, and are positioned with respect to the distal end section of the endoscope to continue from the distal end sections of the first support section 63 and the second support section 64 toward the distal end section of the endoscope so as to be inclined outward in the radial direction of the distal end section of the endoscope. As a result, the first support section 63 and the second support section 64 of the embodiment are positioned with respect to the distal end section of the endoscope so as to be inclined with respect to the first axis C1. For example, the first support section 63 and the second support section 64 of the embodiment are positioned as proximal end sections of a first pressing section 65 and a second pressing section 66 (described below) continuing to the protrusion sections 61 and 62 are attached to the distal end section of the endoscope by a fastener (a positioning section). In this case, the first pressing section 65 and the second pressing section 66 support the protrusion sections 61 and 62 using the distal end sections, and function as a first connecting section and a second connecting section configured to connect the protrusion sections 61 and 62 and the fastener. The first support section 63 extends from the first protrusion section 61 to the proximal end side while inclined by, for example, about 45° with respect to the second axis C2. That is, an angle θ1 of the second axis C2 and the first support section 63 with respect to the proximal end side is about 45°.

The second support section 64 extends from the second protrusion section 62 to the proximal end side while inclined toward the same proximal end side as the first support section 63 with respect to the second axis C2 when seen in the perpendicular direction D perpendicular to the second axis C2. That is, when seen in the perpendicular direction D, the proximal end side of the first support section 63 and the proximal end side of the second support section 64 are disposed at the proximal end side so as to be inclined in the same direction as the second axis C2.

In the embodiment, the support sections 63 and 64 are configured to overlap when seen in a side view shown in FIG. 1 and directed toward the distal end of the endoscope auxiliary tool 60 to approach each other when seen in a plan view shown in FIG. 2. That is, the entire endoscope auxiliary tool 60 is configured so as to be tapered when seen in a plan view shown in FIG. 2.

As shown in FIG. 2, the endoscope auxiliary tool 60 has the first pressing section 65 and the second pressing section 66. The first pressing section 65 is disposed such that a distal end continues to the first protrusion section 61 and extends from the first protrusion section 61 to the proximal side. As shown in FIG. 2, the second pressing section 66 is disposed such that a distal end continues to the second protrusion section 62 and extends from the second protrusion section 62 to the proximal side. That is, the second pressing section 66 is configured to extend from the second protrusion section 62 to the proximal side of the endoscope auxiliary tool 60. The endoscope auxiliary tool 60 includes two sets of protrusion sections, support sections and pressing sections. The above-mentioned support sections 63 and 64 and the pressing sections 65 and 66 are formed in linear shapes. When seen in a plan view shown in FIG. 2, the pressing sections 65 and 66 are configured so as to be directed toward the distal end of the endoscope auxiliary tool 60 to approach each other.

The first protrusion section 61, the first support section 63 and the first pressing section 65 are integrally formed with each other by coating an outer surface of a rod-shaped member formed of stainless steel with a resin or the like having insulation and folding it. Further, the first protrusion section 61, the first support section 63 and the first pressing section 65 may be integrally formed of a resin. The second protrusion section 62, the second support section 64 and the second pressing section 66 are formed in the same way as the first protrusion section 61, the first support section 63 and the first pressing section 65. As shown in FIGS. 1 and 2, the proximal end section of the first pressing section 65 and the proximal end section of the second pressing section 66 are attached to the distal end rigid section 22 of the insertion section 20 by a medical band B (a positioning section such as a fastener or the like) or the like.

The endoscope auxiliary tool 60 is attached to the insertion section 20 such that the protrusion sections 61 and 62 are in the field of vision range R1 of the observation unit 27.

Spacing distances between the first protrusion section 61 and the second protrusion section 62, between the first support section 63 and the second support section 64 and between the first pressing section 65 and the second pressing section 66 are larger than the inner diameter of the channel 21. When seen in the perpendicular direction D, the pressing sections 65 and 66 are disposed at a position slightly deviated from the first axis C1.

As shown in FIG. 1, the endoscope treatment system 1 according to the embodiment is used with a high frequency knife 200 having a treatment tool insertion section 210 that can be inserted into the channel 21.

The high frequency knife 200 has a known configuration, and includes the above-mentioned treatment tool insertion section 210 and a treatment tool manipulation section 220 installed at the proximal end section of the treatment tool insertion section 210.

In the treatment tool insertion section 210, a conductive manipulation wire (not shown) is inserted through a sheath 211 to advance and retreat. A rod-shaped electrode 212 (see FIG. 3) is fixed to the distal end section of the manipulation wire. The electrode 212 extends in a longitudinal direction of the sheath 211. An operator can draw the electrode 212 out of the distal end of the sheath 211 or accommodate the electrode 212 in the sheath 211 by advancing and retracting the manipulation wire with respect to the sheath 211.

The treatment tool manipulation section 220 includes a rod-shaped manipulation section main body 221 fixed to the proximal end section of the sheath 211, and a slider 222. The manipulation section main body 221 includes a finger hooking ring 221a disposed at the proximal end section. The slider 222 is slidably installed in the longitudinal direction of the manipulation section main body 221 with respect to the manipulation section main body 221.

The slider 222 includes the finger hooking rings 222a and 222b arranged in parallel in a direction perpendicular to the longitudinal direction of the manipulation section main body 221. The slider 222 includes a connecting connector section 223 to which a cord passing through a high frequency wave generating apparatus (not shown) is electrically connected.

The connecting connector section 223 is electrically connected to the proximal end section of the manipulation wire.

Next, an operation of the endoscope treatment system 1 configured as described above will be described. Hereinafter, for example, an operation of excising a mucosa in a body cavity using the endoscope treatment system 1 will be described.

First, an operator such as a surgeon or the like mounts an return electrode plate (not shown) on a patient. The operator attaches the endoscope auxiliary tool 60 to the insertion section 20 using the medical band B. Next, the operator starts the endoscope 10 by manipulating the switch 42 to supply power from a power supply to the CCD or the like of the observation unit 27. Illumination light emitted from the light source is supplied to the proximal end surface of the light guide 26, and the illumination light introduced to the light guide 26 is radiated in front of the insertion section 20. The operator introduces the insertion section 20 from the mouth of the patient into the body cavity while observing an image acquired by the observation unit 27 of the endoscope 10 using the monitor.

The operator disposes the distal end surface 22a of the insertion section 20 to oppose the affected mucosa portion serving as a target area so as to be incised in the body cavity when the angle knob 41 is manipulated according to necessity to introduce the insertion section 20 while curving the curved section 23.

In a state in which the position of the distal end surface 22a of the insertion section 20 with respect to the affected mucosa portion is held, the operator introduces an injection needle (not shown) into the body cavity via the forceps port 43 and the channel 21 of the endoscope 10. Next, the operator injects a physiological saline solution into a submucosal layer of an affected mucosa portion P1 shown in FIG. 3 using the injection needle to raise the affected mucosa portion P1. After that, the operator pulls the injection needle out of the channel 21.

The operator grips the treatment tool manipulation section 220 by passing his or her fingers through the ring 221a and the rings 222a and 222b. The operator moves (pulls back) the slider 222 to the proximal side with respect to the manipulation section main body 221 of the high frequency knife 200, and accommodates the electrode 212 in the sheath 211. Next, the operator introduces the treatment tool insertion section 210 of the high frequency knife 200 into the channel 21 of the endoscope 10.

The operator causes the treatment tool insertion section 210 to protrude from the distal end surface 22a of the insertion section 20. Here, as shown in FIGS. 2 and 4, the treatment tool insertion section 210 is disposed on the first axis C1 between the first protrusion section 61 and the second protrusion section 62. Next, the operator connects a cord of the high frequency wave generating apparatus to the connecting connector section 223 of the treatment tool manipulation section 220, and applies a high frequency voltage to the electrode 212 via the manipulation wire.

The operator moves (pushes) the slider 222 toward the distal end with respect to the manipulation section main body 221, and as shown in FIG. 3, causes the electrode 212 to protrude from the distal end of the sheath 211.

Next, the operator places the electrode 212 on the mucosal layer P2 around the affected mucosa portion P1 and a submucosal layer (not shown). The operator moves the electrode 212 in a direction crossing the longitudinal direction of the electrode 212, incises the mucosal layer P2 or the like using the electrode 212, and forms the opening P3 through manipulation or the like of curving the curved section 23.

Next, the operator pulls the high frequency knife 200 back with respect to the endoscope 10 while pulling the slider 222 back with respect to the manipulation section main body 221, and accommodates the treatment tool insertion section 210 in the channel 21.

As shown in FIGS. 4 and 5, the operator introduces the protrusion sections 61 and 62 between the submucosal layer P5 and the muscle layer P6 closer to the affected mucosa portion P1 than an opening P3 through the opening P3 by pushing the insertion section 20 of the endoscope 10 thereinto. Here, the pressing sections 65 and 66 are disposed closer to the muscle layer P6 than the support sections 63 and 64. A surgical field becomes substantially flat as the muscle layer P6 is held by the pressing sections 65 and 66. The support sections 63 and 64 and the pressing sections 65 and 66 are configured to be directed toward the distal end of the endoscope auxiliary tool 60 to approach each other. For this reason, the endoscope auxiliary tool 60 has a tapered shape as a whole, and the endoscope auxiliary tool 60 is easily introduced between the submucosal layer P5 and the muscle layer P6.

The mucosal layer P2 and the submucosal layer P5 (hereinafter referred to as "a lid section P7") dissected from the muscle layer P6 closer to the affected mucosa portion P1 than the opening P3 are supported by the support sections 63 and 64. As the lid section P7 is supported by the pair of support sections 63 and 64, the lid section P7 can be suppressed from entering a space V (see FIG. 4) disposed between the support sections 63 and 64 and closer to the pressing sections 65 and 66 than the support sections 63 and 64. When the lid section P7 comes in contact with the support sections 63 and 64, the lid section P7 is supported by the support sections 63 and 64. For this reason, when the lid section P7 is supported by the support sections 63 and 64, even when the length in a direction along the support sections 63 and 64 of the lid section P7 is smaller than the length of the support sections 63 and 64, the endoscope auxiliary tool 60 can securely support the lid section P7 using the support sections 63 and 64.

As the lid section P7 is supported by the support sections 63 and 64, the operator can securely recognize the connecting portion P8 of the lid section P7 and the muscle layer P6, and the protrusion sections 61 and 62 disposed at the connecting portion P8 using the monitor. The connecting portion P8 is configured to extend in the perpendicular direction D with respect to the endoscope auxiliary tool 60.

Since the protrusion sections 61 and 62 are disposed at positions of the endoscope auxiliary tool 60 closest to the distal end side, the protrusion sections 61 and 62 are disposed at positions close to a connecting portion P8.

The operator pushes the slider 222 into the manipulation section main body 221 while pushing the high frequency knife 200 into the endoscope 10, and causes the electrode 212 to protrude again from the distal end surface 22a of the insertion section 20.

Since the treatment tool insertion section 210 is disposed on the first axis C1, the electrode 212 is sent forward between the first protrusion section 61 and the second protrusion section 62 on the first axis C1. That is, the endoscope auxiliary tool 60 is not disturbed when the operator pushes the high frequency knife 200 into the endoscope 10.

In the connecting portion P8, when the electrode 212 that protrudes forward comes in contact with an intermediate section between a portion near the first protrusion section 61 and a portion near the second protrusion section 62, the connecting portion P8 is incised.

When the operator curves the curved section 23, the endoscope auxiliary tool 60 also swings (shakes) with the distal end rigid section 22. When the endoscope auxiliary tool 60 swings in the perpendicular direction D, the endoscope auxiliary tool 60 or the electrode 212 moves (slides) in the perpendicular direction D with respect to the lid section P7 or the muscle layer P6. In this way, since the operator can swing the endoscope auxiliary tool 60 in the perpendicular direction D while supporting the lid section P7, the operator can continuously and rapidly perform the incision of the connecting portion P8.

Next, the operator incises the connecting portion P8 of the lid section P7 and the muscle layer P6 while pushing the insertion section 20 thereinto and curving the curved section 23, and excises and dissects the affected mucosa portion P1 as a whole.

After that, the operator pulls the slider 222 back to accommodate the electrode 212 in the sheath 211, and pulls the high frequency knife 200 out of the channel 21 of the endoscope 10 to the proximal side. The operator inserts a grasp forceps or the like (not shown) through the channel 21, and manipulates the grasp forceps to remove the affected mucosa portion P1 through the channel 21.

Finally, the operator pulls the insertion section 20 of the endoscope 10 out of the mouth of the patient, and performs necessary treatment to terminate a series of treatment.

As described above, according to the endoscope treatment system 1 of the embodiment, as the lid section P7 is supported by the support sections 63 and 64, the operator can easily recognize the connecting portion P8 of the lid section P7 and the muscle layer P6. Since the protrusion sections 61 and 62 are configured to sandwich the first axis C1 in the perpendicular direction D, when the operator pushes the high frequency knife 200 through which the treatment tool insertion section 210 is inserted into the channel 21, the electrode 212 passes between the first protrusion section 61 and the second protrusion section 62. For this reason, in the connecting portion P8, the electrode 212 that is sent forward comes in contact with the intermediate section between the portion near the first protrusion section 61 and the portion near the second protrusion section 62, and the operator can easily dissect the submucosal layer P5 from the muscle layer P6.

As the endoscope auxiliary tool 60 includes the pressing sections 65 and 66, the muscle layer P6 can be held substantially flat when the connecting portion P8 is incised, and the procedure can be easily performed.

The endoscope auxiliary tool 60 is open between the first support section 63 and the second support section 64 and between the first pressing section 65 and the second pressing section 66. Accordingly, a procedure such as local injection, hemostasis, or the like, is easily performed therebetween, and difficulties in observation by the observation unit 27 due to collection of smoke or the like generated in the space V upon incision using the high frequency knife 200 can be limited.

In the embodiment, while an example in which the endoscope auxiliary tool includes two sets of protrusion sections, support sections and pressing sections has been described, the endoscope auxiliary tool may be configured to include three or more sets of protrusion sections, support sections and pressing sections.

Figure 6:
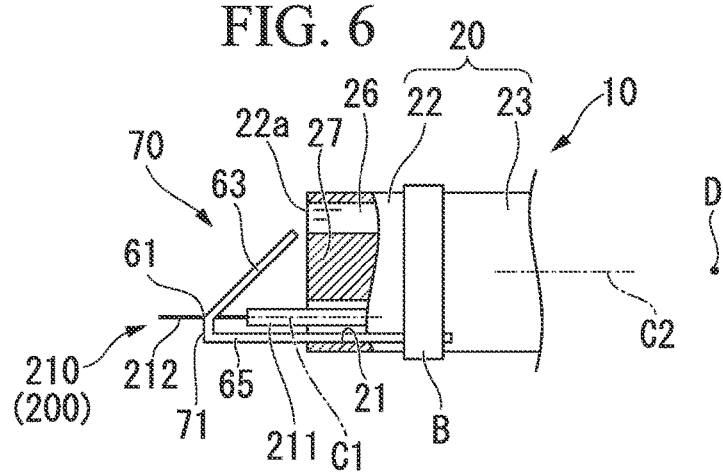
FIG. 6 is a partial cross-sectional view of a side surface of a distal end section in an endoscope treatment system of a first variant of the first embodiment of the present invention.

Like the first variant of the substrate shown in FIG. 6, in addition to the configurations of the endoscope auxiliary tool 60, an endoscope auxiliary tool 70 may include a first connecting section 71 having end sections that continue to the first protrusion section 61 and the first pressing section 65. In the variant, while not shown, the endoscope auxiliary tool 70 also includes a second connecting section having end sections that continue to the second protrusion section 62 and the second pressing section 66. The first connecting section 71 and second connecting section are disposed in parallel to the distal end surface 22a of the insertion section 20.

Even in the first variant, when seen in the perpendicular direction D, the protrusion sections 61 and 62 are disposed on the first axis C1.

As the endoscope auxiliary tool 70 is configured as described above, even when the inner diameter of the channel 21 is large and the outer diameter of the treatment tool insertion section 210 is large, the operator can easily incise the connecting portion P8 of the lid section P7 and the muscle layer P6 using the electrode 212.

Figure 7:
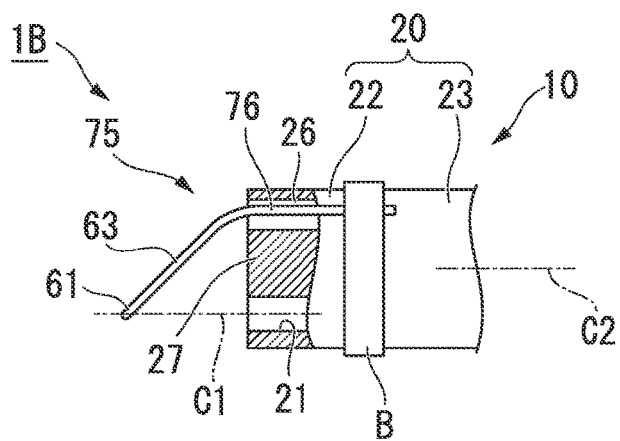
FIG. 7 is a partial cross-sectional view of a side surface of a distal end section of an endoscope treatment system of a second variant of the first embodiment of the present invention.

FIG. 7 is a partial cross-sectional view of a side surface of a distal end section of an endoscope treatment system of a second variant of the first embodiment of the present invention. Like the variant shown in FIG. 7, instead of the pressing sections 65 and 66 of the endoscope auxiliary tool 60, an endoscope auxiliary tool 75 may include a first connecting section 76 and a second connecting section (not shown). The first connecting section 76 is configured to extend to the proximal side of the endoscope auxiliary tool 75 having a distal end section that continues to the proximal end section of the first support section 63. The second connecting section is configured to extend to the proximal side of the endoscope auxiliary tool 75 having a distal end section that continues to the proximal end section of the second support section 64. In the variant, the support sections 63 and 64 are folded so as to be inclined with respect to the axial direction of the first connecting section 76 and/or the second connecting section, and the first connecting section 76 and second connecting section are configured to be attached to the distal end section of the endoscope by the fastener (the positioning section) and inclined with respect to the axial direction of the endoscope (the channel) at a position closer to the distal side than the distal end of the endoscope. In addition, the distal end sections of the first support section 63 and the second support section 64 sandwich the first axis C1 at a position closer to the distal side than the distal end section of the endoscope, and are positioned by the fastener (the positioning section) via the first connecting section 76 and second connecting section with respect to the distal end section of the endoscope to continue from the distal end sections of the first support section 63 and the second support section 64 toward the distal end section of the endoscope and inclined outward in the radial direction of the distal end section of the endoscope. The distal end sections of the support sections 63 and 64 of the variant, i.e., the protrusion sections 61 and 62, can be configured to easily enter the distal end section of the endoscope between the submucosal layer P5 and the muscle layer P6, like the first embodiment.

The proximal end section of the first connecting section 76 and the proximal end section of the second connecting section are attached to the distal end rigid section 22 of the insertion section 20 using the medical band B or the like.

The same effect as in the endoscope treatment system 1 according to the embodiment can be exhibited even by the endoscope treatment system 1B including the endoscope auxiliary tool 75 of the variant configured as described above.

Further, in the endoscope auxiliary tool 75 of the variant, without including both of the connecting sections, the proximal end sections of the support sections 63 and 64 may be directly attached to the distal end rigid section 22 of the insertion section 20.

Second Embodiment

Next, a second embodiment of the present invention will be described with reference to FIGS. 8 and 9. The same components as in the first embodiment of the present invention are designated by the same reference numerals, a description thereof will be omitted, and only different points will be described.

Figure 8:
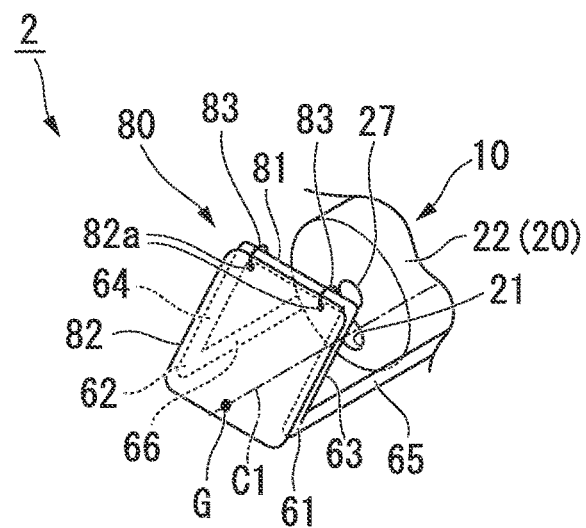
FIG. 8 is a perspective view of a distal end section of an endoscope treatment system according to a second embodiment of the present invention.

As shown in FIG. 8, an endoscope treatment system 2 according to the embodiment includes an endoscope auxiliary tool 80 instead of the endoscope auxiliary tool 60 of the endoscope treatment system 1 according to the first embodiment.

The endoscope auxiliary tool 80 includes a connecting section 81 and a plate-shaped member 82 in addition to the components of the endoscope auxiliary tool 60. The connecting section 81 is connected to the proximal end section of the first support section 63 and the proximal end section of the second support section 64. The plate-shaped member 82 is rotatably supported by the connecting section 81.

Figure 9:
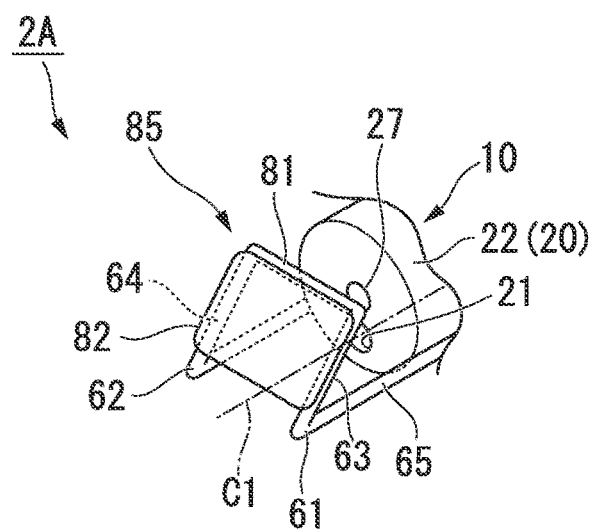
FIG. 9 is a perspective view of a distal end section of an endoscope treatment system of a variant of the second embodiment of the present invention.

In FIG. 8 and FIG. 9 described below, while the support sections 63 and 64 are formed in parallel to each other, the support sections 63 and 64 may be formed so as to be directed toward the distal end of the endoscope auxiliary tool 80 to approach each other. This is also the same in the pressing sections 65 and 66. That is, in FIG. 8 and FIG. 9 described below, while the pressing sections 65 and 66 are formed in parallel to each other, the pressing sections 65 and 66 may be formed so as to be directed downward along the distal end of the endoscope auxiliary tool 80 to approach each other.

Like the first protrusion section 61 or the like, the connecting section 81 may be configured by coating a rod-shaped member formed of stainless steel with a resin. In the embodiment, the protrusion sections 61 and 62, the support sections 63 and 64, the pressing sections 65 and 66 and the connecting section 81 are integrally formed with each other.

The plate-shaped member 82 is formed of a known resin having biocompatibility such as acrylonitrile butadiene styrene (ABS) resin in a rectangular shape. The plate-shaped member 82 may be formed of a transparent material.

A pair of through-holes 82a are formed in an edge section of the plate-shaped member 82 at an interval along the edge section.

The plate-shaped member 82 is disposed closer to the distal end of the endoscope auxiliary tool 80 than the support sections 63 and 64 and the connecting section 81. A thread 83 inserted through the through-hole 82a formed in the plate-shaped member 82 is coupled to the connecting section 81.

As shown in FIG. 8, a position of the plate-shaped member 82 with respect to the support sections 63 and 64 when a surface of the proximal end side of the plate-shaped member 82 abuts the support sections 63 and 64 is defined as a normal position.

When the plate-shaped member 82 is at the normal position, the first axis C1 intersects the surface of the proximal end side of the plate-shaped member 82 at a point G. In other words, the plate-shaped member 82 at the normal position is disposed at a position at which progress of the treatment tool inserted through the channel 21 along the first axis C1 is disturbed.

In the endoscope treatment system 2 configured as described above, when the plate-shaped member 82 is at the normal position and the lid section P7 presses the surface of the distal end side of the plate-shaped member 82 to the proximal side, the plate-shaped member 82 is supported by the support sections 63 and 64 and the connecting section 81. Accordingly, the endoscope treatment system 2 can securely support the lid section P7 using the endoscope auxiliary tool 80. Since the plate-shaped member 82 is formed of a transparent material, the operator can observe the situation more distal than the plate-shaped member 82 through the plate-shaped member 82 using the observation unit 27.

Meanwhile, when the operator pushes the high frequency knife 200 through which the treatment tool insertion section 210 is inserted into the channel 21, the electrode 212 comes in contact with the plate-shaped member 82 at the point G. When the operator further pushes the high frequency knife 200 inward, the plate-shaped member 82 is pivoted around the connecting section 81 as the electrode 212 presses the plate-shaped member 82 toward the distal end, the electrode 212 can be moved further forward than the plate-shaped member 82.

According to the endoscope treatment system 2 of the embodiment having the above-mentioned configuration, the operator can easily dissect the submucosal layer P5 from the muscle layer P6.

While the embodiment shows the configuration in which the plate-shaped member 82 is rotatably supported with respect to the connecting section 81, the embodiment is not limited thereto. For example, as the end section of the plate-shaped member is curved in a tubular shape and the connecting section 81 is inserted through the tube, the plate-shaped member may be rotatably supported by the connecting section 81.

In addition, in the embodiment, as a variant, like an endoscope auxiliary tool 85 shown in FIG. 9, the plate-shaped member 82 may be attached to the support sections 63 and 64 and the connecting section 81 by an adhesive agent or the like (not shown). In the variant, the plate-shaped member 82 is formed at a region that does not include the first axis C1. That is, the plate-shaped member 82 is disposed at a position at which progress of the treatment tool is not disturbed.

In the endoscope treatment system 2A having the above-mentioned configuration, when the lid section P7 presses the surface of the distal end side of the plate-shaped member 82, the plate-shaped member 82 is supported by the support sections 63 and 64 and the connecting section 81. Meanwhile, when the operator pushes the high frequency knife 200 through which the treatment tool insertion section 210 is inserted into the channel 21, the electrode 212 moves further forward than the plate-shaped member 82 through the protrusion sections 61 and 62 side of the plate-shaped member 82. Then, the operator can easily dissect the submucosal layer P5 from the muscle layer P6 using the electrode 212.

In this embodiment, since the plate-shaped member 82 is disposed in an area between the first support section 63 and the second support section 64 and does not include the first axis C1, a space between the first protrusion section 61 and the second protrusion section 62 can be observed by the observation unit 27. For this reason, the plate-shaped member 82 may be formed of an opaque material.

In a variation of embodiment, the endoscope auxiliary tool 85 may not include the connecting section 81, and the plate-shaped member 82 may be configured to be attached to only the support sections 63 and 64.

Third Embodiment

Next, a third embodiment of the present invention will be described with reference to FIGS. 10 to 14. The same components as in the above-mentioned embodiment are designated by the same reference numerals, description thereof will be omitted, and only different points will be described. While description of the endoscope auxiliary tool will be emphasized below, the endoscope auxiliary tool constitutes the endoscope treatment system together with the above-mentioned endoscope 10.

Figure 10:
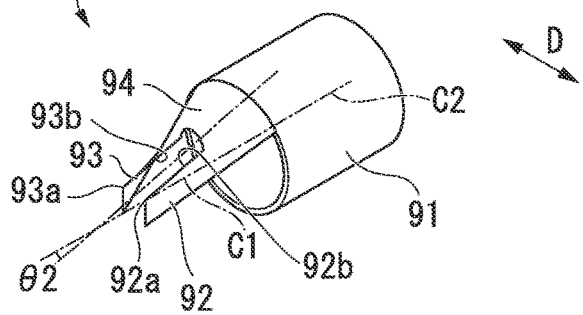
FIG. 10 is a perspective view of an endoscope auxiliary tool according to a third embodiment of the present invention.
Figure 11:
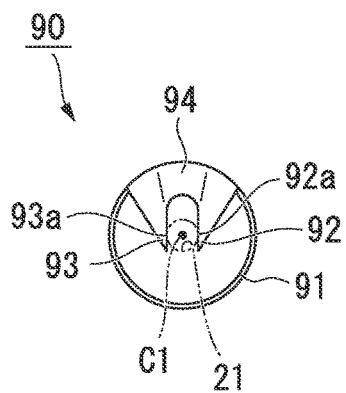
FIG. 11 is a front view of an endoscope auxiliary tool according to the third embodiment of the present invention.

As shown in FIGS. 10 and 11, an endoscope auxiliary tool 90 according to the embodiment includes an attachment member 91, side plates 92 and 93 and a connecting member 94. The attachment member 91 is formed in a tubular shape, and detachably disposed at the distal end rigid section 22 of the insertion section 20 of the endoscope 10. The side plates 92 and 93 are configured to sandwich the first axis C1 at a forward side of the attachment member 91 in the perpendicular direction D. The connecting member 94 connects the side plates 92 and 93 and the attachment member 91.

An inner diameter of the attachment member 91 is slightly larger than an outer diameter of the distal end rigid section 22. A distance between the side plates 92 and 93 is equal to the inner diameter of the channel 21. The connecting member 94 is formed such that a cross-sectional shape perpendicular to the first axis C1 in a direction away from the first axis C1 is a concave arc shape.

The attachment member 91, the side plates 92 and 93 and the connecting member 94 are integrally formed of a resin having insulation properties and biocompatibility such as silicon, polytetrafluoroethylene (PTFE), or the like.

An end of the connecting member 94 side disposed at the distal end section of the side plate 92 is a first protrusion section 92a, and an end of the connecting member 94 side disposed at the distal end section of the side plate 93 is a second protrusion section 93a. An edge section that continues from the first protrusion section 92a of the side plate 92 to extend to the proximal side is a first support section 92b, and an edge section that continues from the second protrusion section 93a of the side plate 93 to extend to the proximal side is a second support section 93b. When the operator attaches the attachment member 91 to the insertion section 20 of the endoscope 10, an angle θ2 formed by the second axis C2 and the support sections 92b and 93b is about 45°.

When the endoscope auxiliary tool 90 having the above-mentioned configuration is attached to the distal end rigid section 22 of the endoscope 10, the first support section 92b, the second support section 93b and the connecting member 94 support the lid section P7. Meanwhile, when the operator pushes the high frequency knife 200 through which the treatment tool insertion section 210 is inserted into the channel 21, the high frequency knife 200 moves the electrode 212 between the side plate 92 and the side plate 93 to a position more distal than the side plates 92 and 93.

Figure 12:
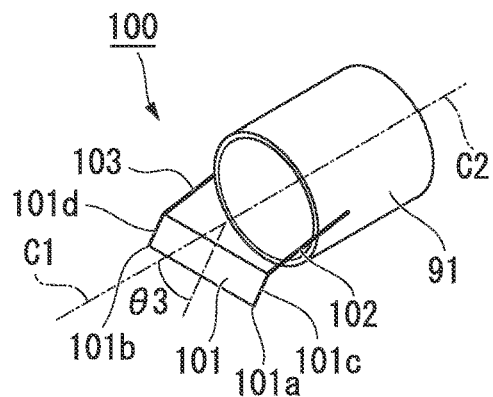
FIG. 12 is a perspective view of an endoscope auxiliary tool of a first variant of the third embodiment of the present invention.

An endoscope auxiliary tool 100 according to a first variant of the embodiment shown in FIG. 12 includes the above-mentioned attachment member 91, a flap 101 and connecting members 102 and 103. The flap 101 is formed in a plate shape, and disposed closer to the distal end than the attachment member 91. The connecting members 102 and 103 are formed in a rod shape, and connect the flap 101 and the attachment member 91.

The flap 101 and the connecting members 102 and 103 may be configured using the same material as the attachment member 91 and the first protrusion section 61. A connecting section between the flap 101 and the connecting members 102 and 103 and a connecting section between the connecting members 102 and 103 and the attachment member 91 are fixed by a known adhesive agent. That is, the flap 101 is fixed to the attachment member 91 by the connecting members 102 and 103.

In the first variant of the embodiment, the end sections in the widthwise direction at the distal end sections of the flap 101 are a first protrusion section 101a and a second protrusion section 101b. An edge section that continues from the first protrusion section 101a of the flap 101 to extend to the proximal side is a first support section 101c, and an edge section that continues from the second protrusion section 101b to extend to the proximal side is a second support section 101d.

When the attachment member 91 is attached to the insertion section 20 of the endoscope 10, an angle θ3 formed by the second axis C2 and the support sections 101c and 101d is about 45°.

Figure 13:
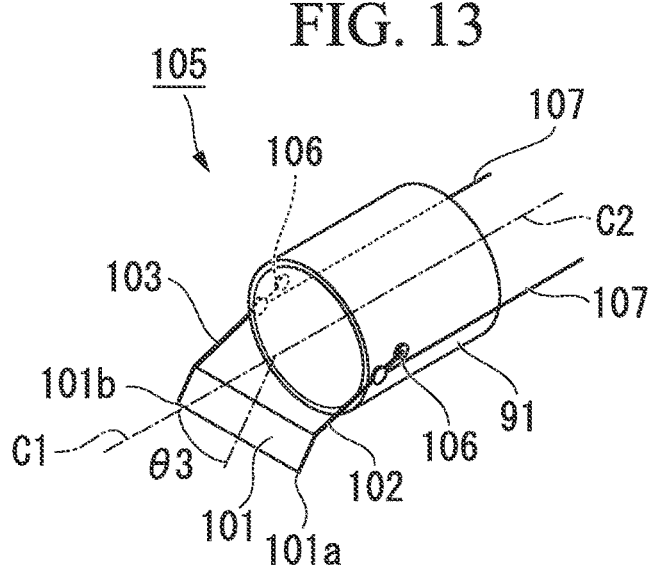
FIG. 13 is a perspective view of an endoscope auxiliary tool of a second variant of the third embodiment of the present invention.

In an endoscope auxiliary tool 105 according to a second variant of the substrate shown in FIG. 13, the proximal end sections of the connecting members 102 and 103 are rotatably connected to the attachment member 91 by a known connecting structure 106. The connecting structure 106 may be constituted by, for example, holes formed in side surfaces of the attachment member 91, and hooks formed at the proximal end sections of the connecting members 102 and 103 and inserted through the above-mentioned holes.

Distal end sections of traction wires 107 are connected to intermediate sections in the longitudinal direction of the connecting members 102 and 103. The traction wire 107 extends to the proximal side of the endoscope auxiliary tool 105.

In the endoscope auxiliary tool 105 having the above-mentioned configuration, the operator can move the flap 101 to adjust the above-mentioned angle θ3 by pulling or pushing the pair of traction wires 107. That is, when the operator pushes the high frequency knife 200 through which the treatment tool insertion section 210 is inserted into the channel 21, the electrode 212 does not pass between the first protrusion section 101a and the second protrusion section 101b. Next, the operator can move the flap 101 such that the electrode 212 passes between the first protrusion section 101a and the second protrusion section 101b, thereby adjusting the above-mentioned angle θ3.

Figure 14:
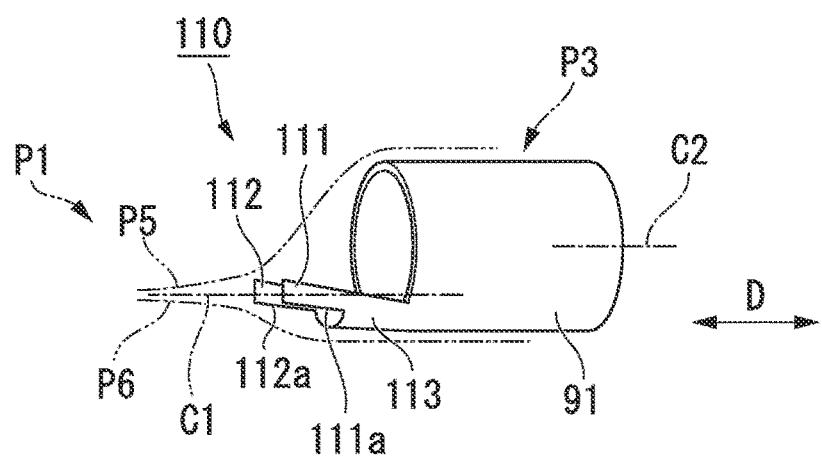
FIG. 14 is a perspective view of an endoscope auxiliary tool of a third variant of the third embodiment of the present invention.

An endoscope auxiliary tool 110 of a third variant of the substrate shown in FIG. 14 includes the above-mentioned attachment member 91, side plates 111 and 112 and a connecting member 113. The side plates 111 and 112 are configured to sandwich the first axis C1 at a forward side of the attachment member 91 in the perpendicular direction D. The connecting member 113 connects the side plates 111 and 112 and the attachment member 91.

An edge section 111a of the side plate 111 and an edge section 112a of the side plate 112 are inclined to approach each other at the outer circumferential surface of the attachment member 91 to the proximal side. The distance between the side plates 111 and 112 is equal to the inner diameter of the channel 21. The connecting member 113 is formed such that a cross-sectional shape perpendicular to the first axis C1 in a direction away from the first axis C1 is a convex arc shape.

The attachment member 91, the side plates 111 and 112 and the connecting member 113 are integrally formed of the same material as the above-mentioned endoscope auxiliary tool 90.

The operator attaches the endoscope auxiliary tool 110 having the above-mentioned configuration to the distal end rigid section 22 of the endoscope 10, and introduces the side plates 111 and 112 between the submucosal layer P5 and the muscle layer P6 through the opening P3. The side plates 111 and 112 are operated to raise the affected mucosa portion P1 from the muscle layer P6.

Next, when the operator pushes the high frequency knife 200 whose treatment tool insertion section 210 is inserted into the channel 21, the electrode 212 moves between the side plate 111 and the side plate 112 to a position more distal than the side plates 111 and 112.

Fourth Embodiment

Next, a fourth embodiment of the present invention will be described with reference to FIGS. 15 to 23. The same components as in the substrate are designated by the same reference numerals, a description thereof will be omitted, and only different points will be described.

Figure 15:
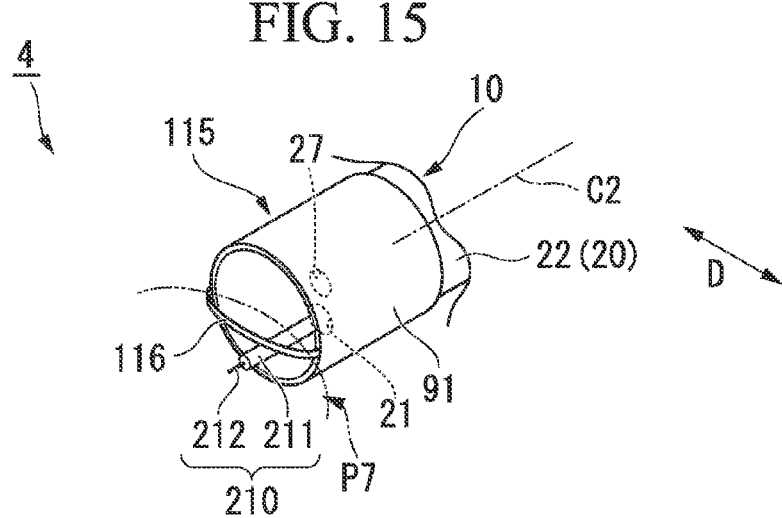
FIG. 15 is a perspective view of a distal end section of an endoscope treatment system according to a fourth embodiment of the present invention.
Figure 16:
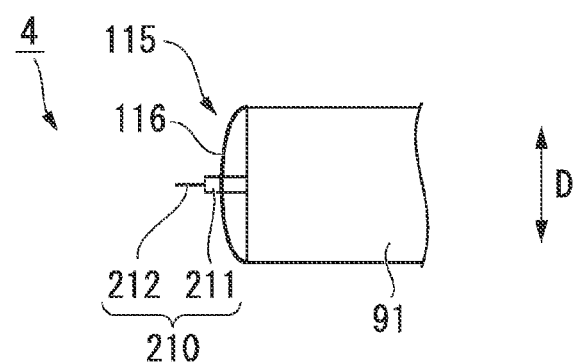
FIG. 16 is a plan view of the distal end section of the endoscope treatment system according to the fourth embodiment of the present invention.

As shown in FIGS. 15 and 16, an endoscope auxiliary tool 115 according to the embodiment includes the above-mentioned attachment member 91, and a bar 116 connected to the opposite edge sections at the distal end section of the attachment member 91.

An endoscope treatment system 4 is constituted by the endoscope auxiliary tool 115 and the endoscope 10.

The bar 116 is curved so as to be convexed toward the distal end of the endoscope auxiliary tool 115. In order to prevent disturbance of the field of vision range R1 of the observation unit 27, the outer diameter of the bar 116 is preferably small. The bar 116 may be formed of the same material as the attachment member 91, or may be formed of the same material as the first protrusion section 61. For example, as the bar 116 is configured using a rod-shaped member formed of stainless steel, which is the same material as the first protrusion section 61, serving as a reinforcement member, the strength of the bar 116 can be increased.

In a front view when the attachment member 91 is attached to the insertion section 20 of the endoscope 10, the bar 116 may be disposed between the channel 21 and the observation unit 27.

Figure 17:
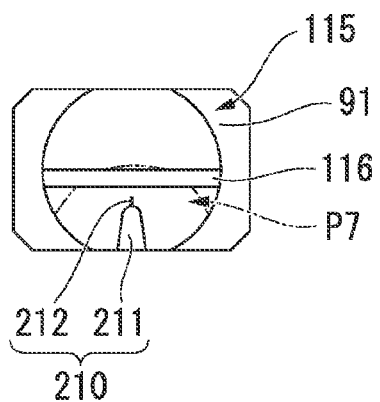
FIG. 17 is a view showing an example of an image displayed on a monitor of the endoscope treatment system according to the fourth embodiment of the present invention.

When a procedure is performed using the endoscope treatment system 4 having the above-mentioned configuration, the operator disposes the channel 21 closer to the muscle layer P6 than the observation unit 27 of the endoscope 10, and as shown in FIGS. 15 and 17, supports the lid section P7 at the observation unit 27 of the bar 116.

Next, when the operator pushes the high frequency knife 200 through which the treatment tool insertion section 210 is inserted into the channel 21 of the endoscope 10, the electrode 212 moves forward without coming in contact with the bar 116.

As the lid section P7 is hooked by the bar 116 to be raised, even when a length in a direction of the second axis C2 of the lid section P7 is relatively small, the lid section P7 can be securely supported by the bar 116.

As the operator swings the endoscope auxiliary tool 115 in a state in which the lid section P7 is raised, the endoscope auxiliary tool 115 or the electrode 212 is moved with respect to the lid section P7 in the perpendicular direction D. For this reason, with no variation in the state in which the lid section P7 is raised, the operator can easily perform incision or dissection.

Figure 18:
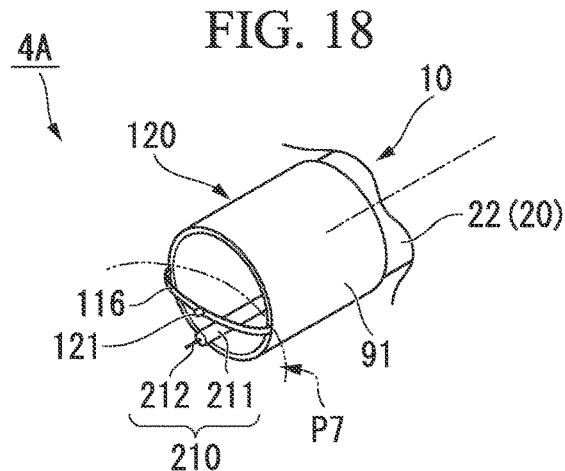
FIG. 18 is a perspective view of a distal end section of an endoscope treatment system of a first variant of the fourth embodiment of the present invention.

An endoscope auxiliary tool 120 of a first variant of the substrate shown in FIG. 18 includes, in addition to the components of the above-mentioned endoscope auxiliary tool 115, a projection 121 protruding toward the distal end of the endoscope auxiliary tool 120 at the central section in the longitudinal direction of the bar 116. The projection 121 may be formed by curving the central section of the rod-shaped member that configures the bar 116 toward the distal end.

Figure 19:
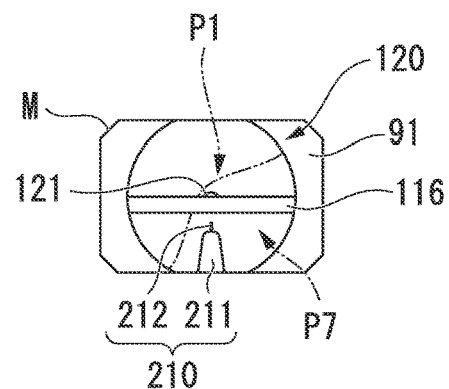
FIG. 19 is a view showing an example of an image displayed on a monitor of the endoscope treatment system of the first variant of the fourth embodiment of the present invention.

When the operator performs the procedure using an endoscope treatment system 4A having the above-mentioned configuration, in an image M shown in FIG. 19 displayed on the monitor, the affected mucosa portion P1 may not be disposed in a 6-o'clock direction. In this case, the bar 116 is largely inclined with respect to the affected mucosa portion P1. Even in this case, as the lid section P7 is hooked by the projection 121, the lid section P7 can be securely raised by the bar 116.

Figure 20:
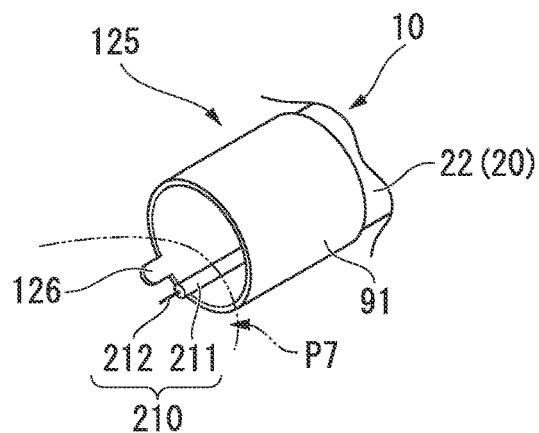
FIG. 20 is a perspective view of a distal end section of an endoscope treatment system of a second variant of the fourth embodiment of the present invention.

An endoscope auxiliary tool 125 of a second variant of a fourth embodiment of the present invention shown in FIG. 20 includes, instead of the bar 116 of the endoscope auxiliary tool 115 according to the embodiment, a projection 126 protruding toward the distal end of the endoscope auxiliary tool 125 at the edge section in the distal end section of the attachment member 91.

Even when the endoscope auxiliary tool 125 is configured in this way, like the endoscope auxiliary tool 120 of the first variant of the above-mentioned fourth embodiment of the present invention, as the lid section P7 is hooked by the projection 126, the lid section P7 can be securely raised by the projection 126.

Figure 21:
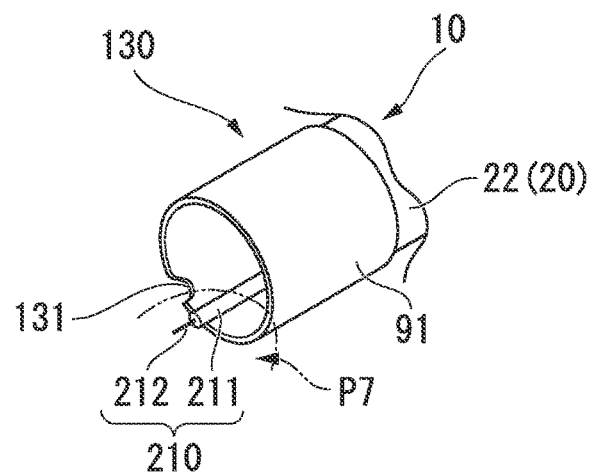
FIG. 21 is a perspective view of a distal end section of an endoscope treatment system of a third variant of the fourth embodiment of the present invention.

An endoscope auxiliary tool 130 of a third variant of the fourth embodiment of the present invention shown in FIG. 21 includes, instead of the projection 126 of the endoscope auxiliary tool 125 of the second variant of the above-mentioned fourth embodiment of the present invention, a concave section 131 concaved from the edge section in the distal end section of the attachment member 91 to the proximal side of the endoscope auxiliary tool 130. The concave section 131 passes a sidewall of the endoscope auxiliary tool 130 in a thickness direction.

Even when the endoscope auxiliary tool 130 is configured in this way, like the endoscope auxiliary tool 125 of the second variant of the above-mentioned fourth embodiment of the present invention, as the lid section P7 is hooked by the concave section 131, the lid section P7 can be securely raised by the concave section 131.

Figure 22:
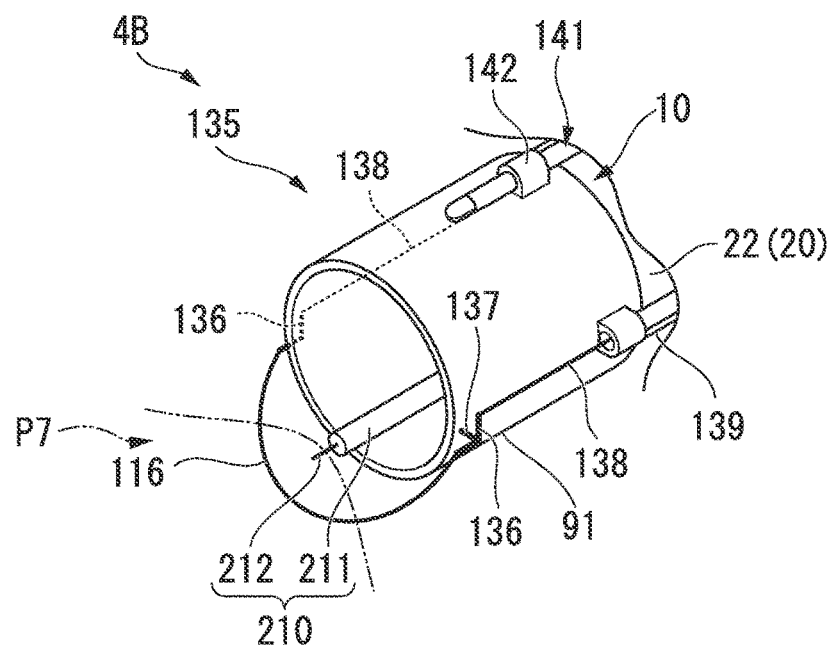
FIG. 22 is a perspective view of a distal end section of an endoscope treatment system of a fourth variant of the fourth embodiment of the present invention.

In an endoscope auxiliary tool 135 of a fourth variant of the fourth embodiment according to the present invention shown in FIG. 22, support shafts 137 fixed to bending sections of L-shaped hook members 136 are rotatably supported at a distal end side of an outer circumferential surface of the attachment member 91. The hook members 136 and the support shafts 137 are disposed in pairs at opposite positions with an axis of the attachment member 91 in the outer circumferential surface of the attachment member 91 interposed therebetween (one of the support shafts 137 is not shown).

End sections of the above-mentioned bar 116 are fixed to one end sections of the hook members 136. Distal end sections of traction wires 138 are connected to the other end sections of the hook members 136. The traction wires 138 extend to the proximal side of the endoscope auxiliary tool 135. Distal end sections of sheaths 139 through which the traction wires 138 are inserted are fixed to the attachment member 91.

A known forceps 141 is supported by a support member 142 at the outer circumferential surface of the attachment member 91 to advance and retreat in the axial direction of the attachment member 91.

When the procedure is performed using the endoscope treatment system 4B configured as described above, as the operator pushes the traction wire 138 inward as shown in FIG. 22, the distal end section of the bar 116 is disposed at a position spaced apart from the support member 142. Manipulation of the traction wires 138 may be performed by an assistant. As some of the manipulation of the endoscope treatment system 4B is allotted to the assistant in this way, the load on the operator can be reduced.

Figure 23:
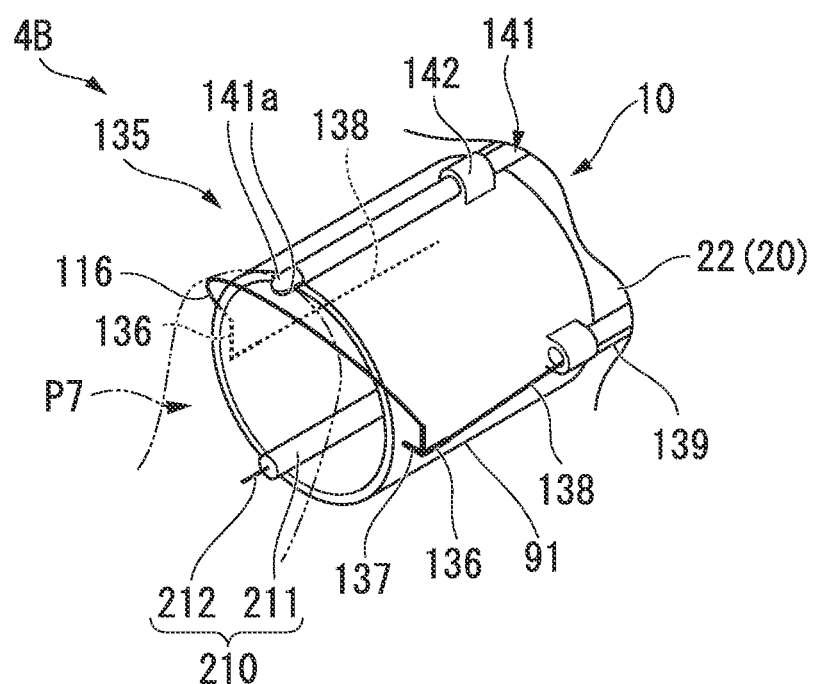
FIG. 23 is a perspective view of the distal end section showing an operation of the endoscope treatment system of the fourth variant of the fourth embodiment of the present invention.

When the operator inserts the bar 116 between the lid section P7 and the muscle layer P6 (not shown) and pulls the traction wires 138 back, the hook members 136 are rotated around the support shaft 137 and the bar 116 is moved as shown in FIG. 23, and the lid section P7 rises in front of the forceps 141.

Next, the operator grips the distal end section of the lid section P7 using a pair of grasp pieces 141a by pushing the forceps 141. In this state, the operator pushes the high frequency knife 200 through which the treatment tool insertion section 210 is inserted into the channel 21, and performs dissection of the connecting portion P8 between the lid section P7 and the muscle layer P6 using the electrode 212.

When the dissection progresses, the operator pushes the forceps 141 that grips the lid section P7 inward and the dissection can be continuously performed even when the affected mucosa portion P1 is large.

Hereinabove, while the first embodiment to the fourth embodiment of the present invention have been described in detail with reference to the accompanying drawings, the specific configuration is not limited to the embodiments but various modifications, combinations, deletions, and so on, may be made without departing from the spirit of the present invention. Further, the configurations shown in the embodiments may be appropriately combined and used.

For example, in the first embodiment and the second embodiment of the present invention, it has been described that the endoscope auxiliary tool is fixed to the insertion section 20 by attaching the proximal end sections of the pressing sections 65 and 66 to the insertion section 20 using the medical band B. However, the endoscope auxiliary tool may be attached to the insertion section 20 by fixing the proximal end sections of the pressing sections 65 and 66 to a tubular attachment member that can be detachably attached to the distal end rigid section 22 of the insertion section 20 using an adhesive agent or the like.

In the first embodiment and the second embodiment of the present invention, it has been described that the support sections 63 and 64 are configured to be directed toward the distal end of the endoscope auxiliary tool to approach each other when seen in a plan view. However, the support sections 63 and 64 may be disposed in parallel to each other. According to the above-mentioned configuration, the distance between the support sections 63 and 64 is not varied regardless of positions in the longitudinal direction of the support sections 63 and 64. Accordingly, the lid section P7 can be securely supported by the support sections 63 and 64. The support sections 63 and 64 may be configured to be directed toward the distal end of the endoscope auxiliary tool so as to be spaced apart from each other (expanded) when seen in a plan view.

The pressing sections 65 and 66 may also be disposed in parallel to each other, and may be configured to be directed toward the distal end of the endoscope auxiliary tool so as to be spaced apart from each other when seen in a plan view.

When seen in a plan view shown in FIG. 2, the support sections 63 and 64 and the pressing sections 65 and 66 may be disposed symmetrically (line symmetrically) with respect to the first axis C1 or may be disposed asymmetrically.

The protrusion sections 61 and 62 have been described as being disposed on the first axis C1 when seen in the perpendicular direction D. However, the positions at which the protrusion sections 61 and 62 are disposed are not limited but the protrusion sections 61 and 62 may be disposed at positions deviated from the first axis C1.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims.

What is claimed is:

1. An endoscope auxiliary tool fixed to a distal end portion of an endoscope, the endoscope auxiliary tool comprising:
   a first rod that includes:
      a distal end and a proximal end;
      a first pressing section that includes the proximal end of the first rod;
      a first support section that includes the distal end of the first rod;
      a first bent section bent between the first pressing section and the first support section;
   a second rod that includes:
      a distal end and a proximal end;
      a second pressing section that includes the proximal end of the second rod;
      a second support section that includes the distal end of the second rod;
      a second bent section bent between the second pressing section and the second support section; and
   a band positioned circumferentially around the distal end portion of the endoscope and which is configured to fix a proximal portion of the first pressing section and a proximal portion of the second pressing section to an outer circumference of the distal end portion of the endoscope,
   wherein:
   when the proximal portion of the first pressing section and the proximal portion of the second pressing section are fixed to the outer circumference of the distal end portion of the endoscope by the band:
      a distal portion of the first pressing section is configured to protrude from a distal end of the endoscope, the distal portion of the first pressing section is configured to extend continuously from the proximal portion of the first pressing section to the first bent section,
      a distal portion of the second pressing section is configured to protrude from a distal end of the endoscope,
      the distal portion of the second pressing section is configured to extend continuously from the proximal portion of the second pressing section to the second bent section,
      the first support section is configured to extend continuously in a direction from the first bent section toward the distal end portion of the endoscope, a distance between the first support section and the first pressing section increasing gradually and continuously in the direction from the first bent section toward the distal end portion of the endoscope, and
      the second support section is configured to extend continuously in a direction from the second bent section toward the distal end portion of the endoscope, a distance between the second support section and the second pressing section increasing gradually and continuously in the direction from the second bent section toward the distal end portion of the endoscope.

2. The endoscope auxiliary tool according to claim 1, further comprising a plate-shaped member attached to each of the first support section and the second support section, and disposed in an area that does not include a center line of the channel.

3. The endoscope auxiliary tool according to claim 2, wherein the plate-shaped member is formed of a transparent material.

4. The endoscope auxiliary tool according to claim 1, wherein a distance between the first bent section and the second bent section is shorter than a distance between the proximal end of the first rod and the proximal end of the second rod.

5. The endoscope auxiliary tool according to claim 4, wherein a distance between the first bent section and the second bent section is shorter than a distance between the distal end of the first rod and the distal end of the second rod.

6. The endoscope auxiliary tool according to claim 1, wherein the first support section and the second support section are positioned in a region more distal than the distal end portion of the endoscope and the first support section and the second support section are inclined with respect to a center line of a channel of the endoscope.

7. An endoscope treatment system comprising: an endoscope which includes a flexible insertion section; and an endoscope auxiliary tool which is fixed to a distal end portion of the insertion section, wherein the endoscope auxiliary tool includes: a first rod that includes: a distal end and a proximal end; a first pressing section that includes the proximal end of the first rod; a first support section that includes the distal end of the first rod; a first bent section being bent between the first pressing section and the first support section; a second rod that includes: a distal end and a proximal end; a second pressing section that includes the proximal end of the second rod; a second support section that includes the distal end of the second rod; a second bent section bent between the second pressing section and the second support section; and
   a band positioned circumferentially around the distal end portion of the insertion section and which is configured to fix a proximal portion of the first pressing section and a proximal portion of the second pressing section to an outer circumference of the distal end portion of the insertion section, wherein: when the proximal portion of the first pressing section and the proximal portion of the second pressing section are fixed to the outer circumference of the distal end portion of the insertion section by the band: a distal portion of the first pressing section is configured to protrude from a distal end of the endoscope, the distal portion of the first pressing section is configured to extend continuously from the proximal portion of the first pressing section to the first bent section, a distal portion of the second pressing section is configured to protrude from a distal end of the endoscope, the distal portion of the second pressing section is configured to extend continuously from the proximal portion of the second pressing section to the second bent section, the first support section is configured to extend continuously in a direction from the first bent section toward the distal end portion of the insertion section, a distance between the first support section and the first pressing section increasing gradually and continuously in the direction from the first bent section toward the distal end portion of the insertion section, and the second support section is configured to extend continuously in a direction from the second bent section toward the distal end portion of the insertion section, a distance between the second support section and the second pressing section increasing gradually and continuously in the direction from the second bent section toward the distal end portion of the insertion section.

8. The endoscope treatment system according to claim 7, wherein a distance between the first bent section and the second bent section is shorter than a distance between the proximal end of the first rod and the proximal end of the second rod.

9. The endoscope treatment system according to claim 8, wherein a distance between the first bent section and the second bent section is shorter than a distance between the distal end of the first rod and the distal end of the second rod.

10. The endoscope treatment system according to claim 7, wherein the first support section and the second support section are positioned in a region more distal than the distal end portion of the insertion section and the first support section and the second support section are inclined with respect to a center line of a channel of the insertion section.

11. The endoscope auxiliary tool according to claim 1, wherein when the proximal portion of the first pressing section and the proximal portion of the second pressing section are fixed to the outer circumference of the distal end portion of the endoscope, the distal end of the first rod and the distal end of the second rod are positioned on opposite sides of a central axis of a channel of the endoscope.

12. The endoscope auxiliary tool according to claim 1, wherein: when the proximal portion of the first pressing section and the proximal portion of the second pressing section are fixed to the outer circumference of the distal end portion of the endoscope, a distance between the first bent section and the second bent section is larger than an inner diameter of a channel of the endoscope, and the distance between the first bent section and the second bent section is smaller than a maximum outer diameter of the distal end portion of the endoscope, and a distance between the first support section and the second support section increases gradually from distal ends of the first support section and the second support section to proximal ends of the first support section and the second support section.

13. The endoscope auxiliary tool according to claim 1, wherein when the proximal portion of the first pressing section and the proximal portion of the second pressing section are fixed to the outer circumference of the distal end portion of the endoscope, the proximal end of the first rod and the proximal end of the second rod are positioned more proximally than a distal end of a channel of the endoscope.

14. The endoscope treatment system according to claim 7, wherein when the proximal portion of the first pressing section and the proximal portion of the second pressing section are fixed to the outer circumference of the distal end portion of the insertion section, the distal end of the first rod and the distal end of the second rod are positioned on opposite sides of a central axis of a channel of the insertion section.

15. The endoscope treatment system according to claim 7, wherein: when the proximal portion of the first pressing section and the proximal portion of the second pressing section are fixed to the outer circumference of the distal end portion of the insertion section, a distance between the first bent section and the second bent section is larger than an inner diameter of a channel of the insertion section, and the distance between the first bent section and the second bent section is smaller than a maximum outer diameter of the distal end portion of the insertion section, and a distance between the first support section and the second support section increases gradually from distal ends of the first support section and the second support section to proximal ends of the first support section and the second support section.

16. The endoscope treatment system according to claim 7, wherein when the proximal portion of the first pressing section and the proximal portion of the second pressing section are fixed to the outer circumference of the distal end portion of the insertion section, the proximal end of the first rod and the proximal end of the second rod are positioned more proximally than a distal end of a channel of the insertion section.

17. The endoscope auxiliary tool according to claim 1, wherein: the first support section is inclined by substantially 45 degrees with respect to a center line of a channel of the endoscope in a direction from a distal end of the first support section to a proximal end of the first support section, and the second support section is inclined by substantially 45 degrees with respect to the center line of the channel of the endoscope in a direction from a distal end of the second support section to a proximal end of the second support section.

18. The endoscope treatment system according to claim 7, wherein: the first support section is inclined by substantially 45 degrees with respect to a center line of a channel of the insertion section in a direction from a distal end of the first support section to a proximal end of the first support section; and the second support section is inclined by substantially 45 degrees with respect to the center line of the channel of the insertion section in a direction from a distal end of the second support section to a proximal end of the second support section.

19. The endoscope auxiliary tool according to claim 1, wherein the second rod is a separate member from the first rod.

20. The endoscope treatment system according to claim 7, wherein the second rod is a separate member from the first rod.

* * * * *